US008524047B2

(12) United States Patent
Ogawa et al.

(10) Patent No.: US 8,524,047 B2
(45) Date of Patent: Sep. 3, 2013

(54) METHOD OF DEHYDRATING TOLYLENEDIAMINE AND DEHYDRATOR

(75) Inventors: Toshiyuki Ogawa, Yokohama (JP); Mitsunaga Dohzaki, Omuta (JP); Masaaki Sasaki, Kashima (JP)

(73) Assignee: Mitsui Chemicals Inc., Tokyo (JP)

( * ) Notice: Subject to any disclaimer, the term of this patent is extended or adjusted under 35 U.S.C. 154(b) by 411 days.

(21) Appl. No.: 12/744,670

(22) PCT Filed: Nov. 25, 2008

(86) PCT No.: PCT/JP2008/071325
§ 371 (c)(1),
(2), (4) Date: May 25, 2010

(87) PCT Pub. No.: WO2009/069584
PCT Pub. Date: Jun. 4, 2009

(65) Prior Publication Data
US 2010/0243423 A1 Sep. 30, 2010

(30) Foreign Application Priority Data
Nov. 27, 2007 (JP) .................................. 2007-306093

(51) Int. Cl.
*C07C 53/08* (2006.01)
(52) U.S. Cl.
USPC .............. 203/14; 203/12; 203/71; 203/75; 203/76; 203/78; 203/79; 203/80; 203/82; 203/83; 203/84
(58) Field of Classification Search
USPC ............. 202/158–161; 203/12, 14, 71, 75, 203/76, 78, 79, 80, 82, 83, 84, 85, 95, 98
See application file for complete search history.

(56) References Cited

U.S. PATENT DOCUMENTS

| 3,420,752 | A | * | 1/1969 | Park et al. ..................... 203/94 |
| 3,421,983 | A | * | 1/1969 | Buchsbaum .................... 203/14 |
| 4,247,653 | A | * | 1/1981 | Wagner ......................... 521/158 |
| 4,717,774 | A | | 1/1988 | Narayan et al. |
| 4,720,326 | A | | 1/1988 | Beckhaus et al. |
| 5,449,832 | A | | 9/1995 | Van Court Carr et al. |
| 5,714,634 | A | * | 2/1998 | Casale et al. .................. 564/422 |
| 5,728,880 | A | * | 3/1998 | Beckhaus et al. ............. 564/305 |
| 5,849,947 | A | * | 12/1998 | Biskup et al. .................. 560/347 |
| 6,472,564 | B1 | * | 10/2002 | Biskup et al. ................. 564/422 |
| 7,307,190 | B2 | * | 12/2007 | Pennemann et al. .......... 564/347 |
| 2004/0222077 | A1 | * | 11/2004 | Yada et al. ........................ 203/1 |
| 2005/0263385 | A1 | * | 12/2005 | Steffens et al. ................. 203/14 |

FOREIGN PATENT DOCUMENTS

| GB | 1 303 562 | 1/1973 |
| JP | 62-045567 A | 2/1987 |
| JP | 62-212351 A | 9/1987 |
| JP | 08-119910 A | 5/1996 |
| JP | 09-052873 A | 2/1997 |

OTHER PUBLICATIONS

Communication (Supplementary European Search Report) in EP Appln No. 08854543.9, dated Jun. 16, 2011.

* cited by examiner

*Primary Examiner* — Duane Smith
*Assistant Examiner* — Thomas McKenzie
(74) *Attorney, Agent, or Firm* — Foley & Lardner LLP

(57) ABSTRACT

A method of dehydrating tolylenediamine which includes subjecting tolylenediamine having a water content of 5-40 wt. % to first-stage distillation at a vacuum of 13-101.3 kPa and subjecting the bottoms from the first-stage distillation to second-stage distillation at a vacuum lower than 13 kPa.

4 Claims, 1 Drawing Sheet

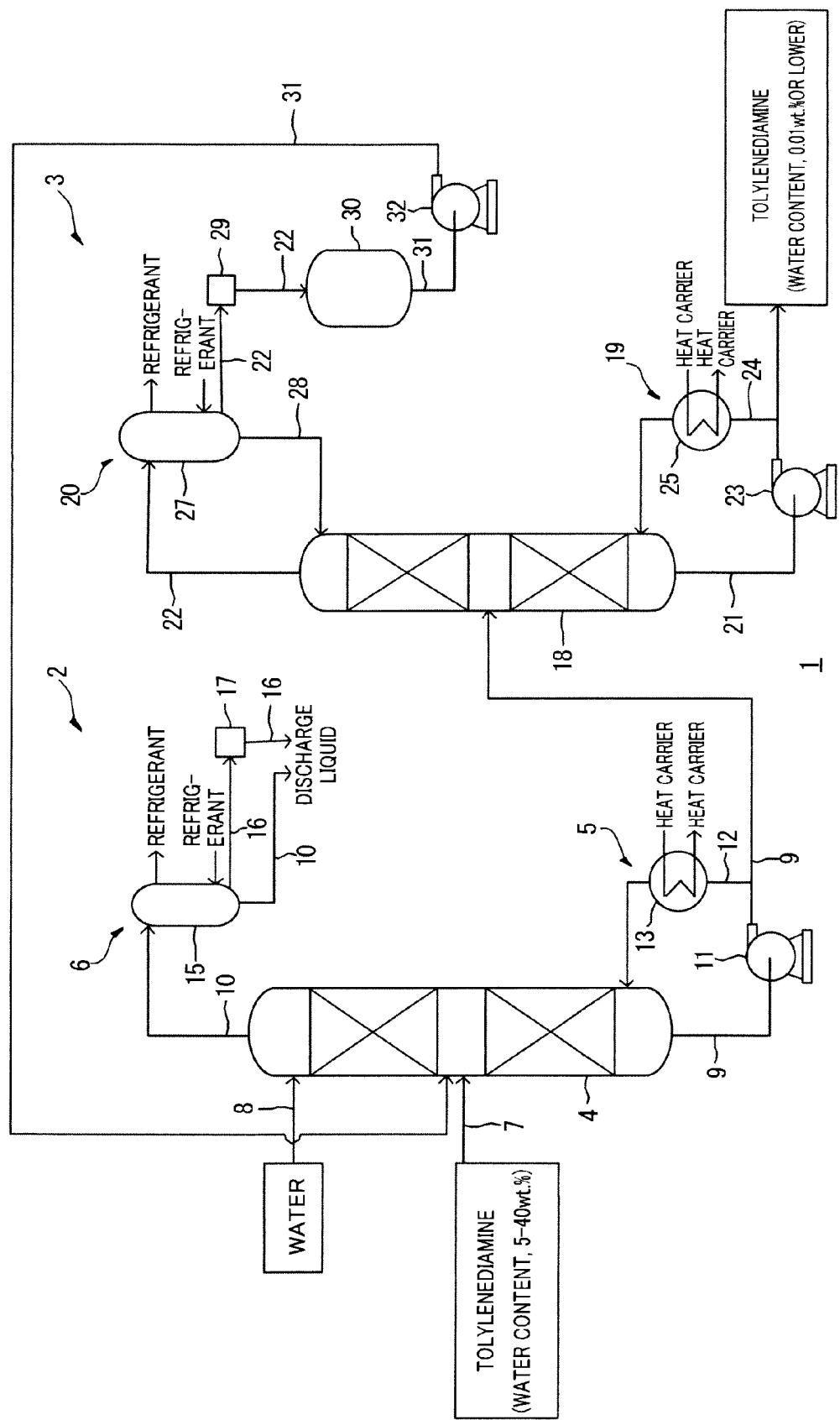

8,524,047 B2

METHOD OF DEHYDRATING TOLYLENEDIAMINE AND DEHYDRATOR

TECHNICAL FIELD

The present invention relates to a method of dehydrating tolylenediamine and a dehydrator, and more particularly, to a method of dehydrating available tolylenediamine having a water content of 5 to 40% by weight, and a dehydrator suitably used for the dehydration method.

BACKGROUND ART

Tolylene diisocyanate, which is important for a raw material of polyurethane, has been industrially produced.

With a production plant for tolylene diisocyanate, tolylene diisocyanate is produced in the following manner. First, toluene as a raw material is dinitrated to produce dinitrotoluene, and the dinitrotoluene is subsequently reduced to produce tolylenediamine. Thereafter, the tolylenediamine is phosgenated to thereby produce tolylene diisocyanate.

However, in this production plant for tolylene diisocyanate, tolylene diisocyanate is produced to satisfy demand, and when the demand for tolylene diisocyanate is high, its production from toluene as the raw material may not be finished on time in some cases. In such case, it is effective to obtain tolylenediamine which is an intermediate raw material, and then produce tolylene diisocyanate from the tolylenediamine.

Such available tolylenediamine is prepared to have a water content of 5 to 15% by weight for storage and transportation (see, for example, the following Patent Document 1).

There has been proposed a method of dehydrating an aqueous solution containing about 60% by weight of diaminotoluene by distillation until it has a residual water content of 3.5% by weight, as a distillation method for separating amine from an amine aqueous solution (see, for example, the following Patent Document 2).

Further, there has been proposed a method for producing toluylene diisocyanate in the following manner. In a first production plant, first, toluene is used as a starting material to form dinitrotoluene, the dinitrotoluene thus formed is hydrogenated to thereby generate a crude solution of toluylene diamine and reaction water, the crude solution of toluylene diamine and reaction water is distilled to yield an intermediate mixture of toluylene diamine and water so that the water content in the intermediate mixture is about 1 to 40% by weight, and the intermediate mixture is transported to a second production plant.

Then, in the second production plant, the intermediate mixture is distilled to yield dry toluylene diamine, and followed by phosgenation of the toluylene diamine to give toluylene diisocyanate (see, for example, the following Patent Document 3).

In this production method, for example, the intermediate mixture of toluylene diamine and water is distilled in a first-stage distillation column to give toluylene diamine having a water content of about 7% by weight, and the toluylene diamine having a water content of about 7% by weight is distilled in a second-stage distillation column to thereby yield toluylene diamine having a water content of 400 ppm.

Patent Document 1: Japanese Unexamined Patent Publication No. 08-119910
Patent Document 2: Japanese Unexamined Patent Publication No. 62-212351
Patent Document 3: Japanese Unexamined Patent Publication No. 09-52873

DISCLOSURE OF THE INVENTION

Problems to be Solved

However, in recent production of tolylene diisocyanate, during phosgenation of tolylenediamine, there has been a need for tolylenediamine to have a water content of 400 ppm or lower (e.g., 100 ppm or less, or preferably 50 ppm or less) currently disclosed in the above-mentioned Patent Document 3 in order to prevent corrosion of an apparatus or to improve quality.

On the other hand, since available tolylenediamine is prepared to have a water content of 5 to 15% by weight for storage and transportation as disclosed in the above-mentioned Patent Document 1, it is necessary to dehydrate the tolylenediamine to have the above-mentioned level of water content in order to use the tolylenediamine as an intermediate raw material of tolylene diisocyanate.

Further, in order to tolerate degradation due to long term transport, the available tolylenediamine as disclosed in the above-mentioned Patent Document 1 is obtained by adding desalted water, deionized water, or distilled water to substantially anhydrous tolylenediamine after purification by distillation, and the tolylenediamine, which has already been purified by distillation, has a higher freezing point than tolylenediamine containing impurities.

As proposed in the above-mentioned Patent Documents 2 and 3, it has been known that tolylenediamine can be dehydrated by distillation. A distillation column used for such distillation is usually designed by calculating the number of theoretical plates according to vapor-liquid equilibrium relationship between the components to be separated by distillation.

Then, it has been attempted that a distillation column capable of dehydrating tolylenediamine having a water content of 5 to 15% by weight by distillation so that the water content of the tolylenediamine reaches the above-mentioned level is designed by calculating the number of theoretical plates according to vapor-liquid equilibrium relationship between water and tolylenediamine. During actual distillation, however, an intermolecular force generated by hydrogen bonding between tolylenediamine and water will act. Therefore, when tolylenediamine is attempted to be dehydrated until the water content thereof reaches the above-mentioned level, an efficient distillation is extremely difficult, such as a region below the freezing point, i.e., a solidification zone, is disadvantageously produced in the distillation column.

In order to prevent the solidification zone from being produced, addition of an azeotropic component or a solvent has been considered. Such addition can however increase in cost of the distillation column.

It is an object of the present invention to provide a method of dehydrating tolylenediamine, the method capable of efficiently dehydrating available tolylenediamine having a water content of 5 to 40% by weight by distillation without producing a solidification zone, and a dehydrator suitably used for the dehydration method.

Means for Solving the Problem

To achieve the above object, the method of dehydrating tolylenediamine according to the present invention includes subjecting tolylenediamine having a water content of 5 to 40% by weight to first-stage distillation at a vacuum degree of 13 to 101.3 kPa, and subjecting bottoms from the first-stage distillation to second-stage distillation at a vacuum degree of less than 13 kPa.

In this method, tolylenediamine is dehydrated by two-stage distillation at specific vacuum degrees, so that in the first-stage distillation, tolylenediamine is dehydrated in a region where tolylenediamine does not solidify, and subsequently, in the second-stage distillation, the tolylenediamine can be dehydrated until the water content thereof reaches a level required for an intermediate raw material of tolylene diisocyanate. Accordingly, the distillation can prevent a solidification zone from being produced and enables tolylenediamine to be dehydrated until the water content thereof reaches a level required for an intermediate raw material of tolylene diisocyanate.

In the method of dehydrating tolylenediamine according to the present invention, it is preferable that the distillate from the second-stage distillation is refluxed to the first-stage distillation.

In this method, since the distillate from the second-stage distillation is refluxed to the first-stage distillation, the distillate from the second-stage distillation is effectively used, so that tolylenediamine remaining in this distillate can be redistilled in the first-stage distillation to recover tolylenediamine.

The distillate from the second-stage distillation contains, for example, tolylenediamine and low-boiling impurities. Since such distillate has a high COD (chemical oxygen demand), a processing apparatus for reducing COD is required in order to discharge the distillate as a drainage. In addition, corresponding to a period of operation (distillation), it is necessary to maintain the processing apparatus during the period, which results in increase in cost.

In this method, however, since the distillate from the second-stage distillation is refluxed to the first-stage distillation without discharging the distillate as a drainage, the effective use of the distillate from the second-stage distillation can achieve reduction in facility cost and operating cost.

In the method of dehydrating tolylenediamine according to the present invention, it is preferable that the bottoms from the first-stage distillation has a water content of less than 1% by weight.

In this method, since the bottoms from the first-stage distillation has a water content of less than 1% by weight, the bottoms can be effectively dehydrated until the water content thereof reaches a level required for an intermediate raw material of tolylene diisocyanate in the second-stage distillation. In addition, in the second-stage distillation, the distillation column can be designed small in size.

In the method of dehydrating tolylenediamine according to the present invention, it is preferable that water is fed to a top portion of a first-stage distillation column in the first-stage distillation.

In this method, in the first-stage distillation column, water is fed to the top of the first-stage distillation column instead of refluxing from a cooling device, to thereby obtain the same effect as the refluxing. Therefore, the steam in the first-stage distillation column can be cooled without providing the first-stage distillation column with a reflux line from the cooling device. As a result, the structure can be simplified, which in turn can achieve improvement in operation, simplification of equipment management, reduction of facility cost, and removal of the tolylenediamine or low-boiling impurities of the distillate.

In the method of dehydrating tolylenediamine according to the present invention, it is preferable that an ejector or a water ring pump is used as a vacuum generator for depressurizing in the second-stage distillation.

When an ejector or a water ring pump is used as the vacuum generator for depressurizing in the second-stage distillation, mixing of oil into the distillate from the second-stage distillation can be prevented. The distillate from the second-stage distillation and condensed water of the steam discharged from the ejector are mixed, so that all or part of the mixture can be redistilled in the first-stage distillation. Alternatively, the distillate from the second-stage distillation and water discharged from the water ring pump are mixed, so that all or part of the mixture can be redistilled in the first-stage distillation.

The dehydrator for tolylenediamine according to the present invention includes a first-stage distillation column; a second-stage distillation column for distilling bottoms from the first-stage distillation column 2; and a reflux units for refluxing the distillate from the second-stage distillation column to the first-stage distillation column 2, the second-stage distillation column produced with an ejector or a water ring pump as a vacuum generator for depressurizing in the column.

With this apparatus, tolylenediamine can be dehydrated by two-stage distillation, so that in the first-stage distillation column 2, tolylenediamine is dehydrated at a level at which tolylenediamine does not solidify, subsequently, in the second-stage distillation column, tolylenediamine can be dehydrated until the water content thereof reaches a level required for an intermediate raw material of tolylene diisocyanate. Accordingly, the distillation can prevent a solidification zone from being produced and enables tolylenediamine to be dehydrated until the water content thereof reaches a level required for an intermediate raw material of tolylene diisocyanate.

With this apparatus, since the distillate from the second-stage distillation column is refluxed to the first-stage distillation column 2 by reflux units, the distillate from the second-stage distillation column is effectively used, so that tolylenediamine remaining in the distillate can be redistilled in the first-stage distillation column 2 to strip tolylenediamine.

Further, with this apparatus, since the distillate from the second-stage distillation column is refluxed to the first-stage distillation column 2 by reflux units without discharging the distillate as a drainage, the effective use of the distillate from the second-stage distillation column can achieve reduction in facility cost and operating cost.

Further, since this apparatus is provided with an ejector or a water ring pump as the vacuum generator for depressurizing in the second-stage distillation column, mixing of oil into the distillate from the second-stage distillation column can be prevented. The distillate from the second-stage distillation column and condensed water of the steam discharged from the ejector are mixed, so that all or part of the mixture can be redistilled in the first-stage distillation column 2. Alternatively, the distillate from the second-stage distillation column and water discharged from the water ring pump are mixed, so that all or part of the mixture can be redistilled in the first-stage distillation column 2.

In the dehydrator of the present invention, it is preferable that the dehydrator for tolylenediamine according to the present invention further includes a water feed units for feeding water to the top portion of the first-stage distillation column 2.

With the dehydrator, in the first-stage distillation column, water is fed from a water feed units to the top of the first-stage distillation column instead of refluxing from a cooling device, to thereby obtain the same effect as the refluxing. Therefore, the steam in the first-stage distillation column can be cooled without providing the first-stage distillation column with a reflux line from the cooling device. As a result, the structure can be simplified, which in turn can achieve improvement in operation, simplification of equipment management, reduction of facility cost, and removal of the tolylenediamine or low-boiling impurities of the distillate.

Effect of the Invention

According to the method of dehydrating tolylenediamine and the dehydrator of the present invention, the distillation can prevent a solidification zone from being produced and enables tolylenediamine to be dehydrated until the water content thereof reaches a level required for an intermediate raw material of tolylene diisocyanate.

BRIEF DESCRIPTION OF THE DRAWINGS

FIG. 1 is a schematic configuration diagram of an embodiment of the tolylenediamine dehydrator of the present invention for performing the method of dehydrating tolylenediamine according to the present invention.

EMBODIMENT OF THE INVENTION

FIG. 1 is a schematic configuration diagram of an embodiment of the tolylenediamine dehydrator of the present invention for performing the method of dehydrating tolylenediamine according to the present invention.

In FIG. 1, this dehydrator 1 includes a first-stage distillation column 2 and a second-stage distillation column 3.

The first-stage distillation column 2 is, for example, a continuous distillation column and more specifically includes a first column main body 4, a first reboiler 5, and a first condenser 6.

The first column main body 4 is, for example, a plate column or a packed column, for example, having packing materials packed inside. Examples of the packing materials include irregular packing materials such as Raschig ring, Lessing ring, Berl saddle, Interlock saddle, Tellerette, Dixon ring, Mcmahon packing, Pall ring, Flexi-ring, Cascade mini-ring, and Intalox metal tower packings; and regular packing materials such as Sulzer packing, Techno-Pack, Dual Pack, and Montz Pack. The first column main body 4 is, if necessary, provided with a distributor, which is not shown, in the midway of its inner portion in the up and down direction. The first column main body 4 is designed with a column diameter of 300 to 3000 mm and 2 to 40 theoretical plates, or more specifically 3 to 20 theoretical plates.

A hydrous tolylenediamine feed pipe 7 for feeding tolylenediamine having a water content of 5 to 40% by weight is connected in the midway of the first column main body 4 in the up and down direction. In addition, a water feed pipe 8 as a water feed units for feeding water is connected on the column top side (the top portion of the first column main body 4) in the midway of the first column main body 4 in the up and down direction. The bottom of the first column main body 4 is connected to a first bottoms extraction pipe 9 for extracting first bottoms which are rich in tolylenediamine. The top of the first column main body 4 is connected to a first distillate extraction pipe 10 for extracting a first distillate which is rich in water. A second reflux pipe 31 (to be described later) is connected in the midway of the first column main body 4 in the up and down direction.

The water feed pipe 8 is connected to a feed water equipment, which is not shown, at its end portion on the upstream side (hereinafter, "upstream side" and "downstream side" are relative to a flow direction of fluid unless otherwise noted).

The first reboiler 5 includes the first bottoms extraction pipe 9, a first bottoms extraction pump 11 interposed in the midway of the first bottoms extraction pipe 9, a first circulation line 12 branching from the first bottoms extraction pipe 9 on the downstream side from the interposed portion of the first bottoms extraction pump 11 to be connected to the bottom of the first column main body 4, and a first heater 13 interposed in the midway of the first circulation line 12.

The first bottoms extraction pump 11 is selected according to the required flow rate of fluid fed and lift as long as the pump is capable of circulating a part of the first bottoms from the bottom of the first column main body 4 to the bottom of the first column main body 4 through the first circulation line 12, and feeding the remainder of the first bottoms from the bottom of the first column main body 4 to the second-stage distillation column 3 through the first bottoms extraction pipe 9, though not particularly limited thereto. Examples thereof include an axial-flow pump, a centrifugal pump, a gear pump, and a diaphragm pump. Among them, a centrifugal pump is preferably used.

The first heater 13 is composed of a heat exchanger and examples thereof include a wetted-wall heat exchanger, a multi-tubular heat exchanger, a coiled heat exchanger, and a jacket heat exchanger. Among them, a wetted-wall heat exchanger or a multi-tubular heat exchanger is preferably used.

A heat medium is fed to the first heater 13, and the amount of the heat medium fed controls the heating temperature of the first heater 13.

In the first reboiler 5, the heating temperature is controlled by the heat medium in the first heater 13 to heat the first bottoms to be circulated through the first circulation line 12 by forced circulation.

For example, a thermo-siphon-type reboiler can also be used as the first reboiler 5. When a thermo-siphon-type reboiler is used as the first reboiler 5, the above-mentioned first bottoms extraction pump 11 is interposed in the first bottoms extraction pipe 9 on the downstream side from the branching portion, though not shown.

The first condenser 6 includes the first distillate extraction pipe 10, a first cooler 15 interposed in the midway of the first distillate extraction pipe 10, a first vacuum line 16 connected to the first cooler 15 on the downstream side separately from the first distillate extraction pipe 10, and a first vacuum generator 17 interposed in the midway of the first vacuum line 16.

The first cooler 15 is composed of a heat exchanger, and examples thereof include a partitioned heat exchanger and a direct contact heat exchanger. Among them, a partitioned heat exchanger is preferably used, or a multi-tubuler heat exchanger or a plate type heat exchanger is more preferably used as a partitioned heat exchanger. A refrigerant is fed to the first cooler 15 and the amount of the refrigerant fed controls the cooling temperature of the first cooler 15.

Examples of the first vacuum generator 17 include vacuum pumps such as a liquid ring vacuum pump, an oil sealed rotary vacuum pump, a Roots vacuum pump, an oil diffusion vacuum pump, a turbo-molecular vacuum pump, cryopump, and a sputter ion pump; and ejectors such as a steam ejector. As described later, since the first distillate is substantially water, a water ring pump as a liquid ring vacuum pump or a steam ejector is preferably used.

In the first condenser 6, cooling temperature is controlled by the refrigerant in the first cooler 15, and a distillate gas from the top of the first column main body 4 is cooled and condensed to form a condensate rich in water, substantially, condensate water (water). The first column main body 4 is depressurized through the first vacuum line 16, the first cooler 15, and the first distillate extraction pipe 10 from the first vacuum generator 17.

In the first-stage distillation column 2, the bottom portion of the first column main body 4 is heated by the first reboiler 5, and the top portion thereof is depressurized by the first condenser 6. This sets the temperature at the bottom portion of the first column main body 4 to, for example, 150 to 250° C., the temperature at the top thereof to, for example, 60 to 100° C., and the vacuum degree to 13 to 101.3 kPa, or preferably 20 to 50 kPa.

Then, the tolylenediamine having a water content of 5 to 40% by weight is fed from the hydrous tolylenediamine feed pipe 7, and water is fed from the water feed pipe 8.

The tolylenediamine fed to the first column main body 4 through the hydrous tolylenediamine feed pipe 7 is an available hydrous tolylenediamine (a mixture of water and tolylenediamine) containing water. The tolylenediamine is not particularly limited as long as it contains water in a predetermined content, and examples thereof include hydrous tolylenediamine obtained by adding water to substantially anhydrous tolylenediamine for storage and transportation as in the above-mentioned Patent Document 1; and hydrous tolylenediamine having the water content adjusted by removing some reaction water from a crude solution of tolylenediamine and reaction water for transportation, the crude solution formed by hydrogenation of dinitrotoluene as in the above-mentioned Patent Document 3.

Tolylenediamine is obtained by a known method, for example, by allowing toluene to react with nitric acid to yield dinitrotoluene and hydrogenating the dinitrotoluene. Tolylenediamine contains, for example, a mixture of various tolylenediamine isomers and, more specifically, primarily contains a mixture of 2,4-tolylenediamine and 2,6-tolylenediamine. As the isomer ratio (molar ratio) of each tolylenediamine in the mixture, for example, the molar ratio of 2,4-tolylenediamine/2,6-tolylenediamine is 19/81 to 21/79.

The tolylenediamine may contain low boiling impurities secondarily produced by a hydrogenation reaction of dinitrotoluene. Examples of the low boiling impurities include 2,3-tolylenediamine and 3,4-tolylenediamine which are isomers other than the above-mentioned isomers, and toluidine.

The water fed from the water feed pipe 8 is not particularly limited and examples thereof include pure water such as deionized water and distilled water; and recovery water (including wastewater). In addition to them, all or part of the water in the first distillate (to be described later) can be used with or without being processed.

As described above, instead of refluxing water from the first condenser 6, feeding of water from the water feed pipe 8 can obtain the same effect as the refluxing, whereby heat efficiency can be improved.

The tolylenediamine having a water content of 5 to 40% by weight is fed at a feed temperature of 50 to 120° C. with a feed rate of 1 to 50 m³/h, and water is fed at a feed temperature of 10 to 60° C. with a feed rate of 0.005 to 2 m³/h depending on the required cooling temperature and reflux rate.

The water content of the tolylenediamine fed to the first column main body 4 through the hydrous tolylenediamine feed pipe 7 ranges from 5 to 40% by weight, or preferably from 5 to 15% by weight. Of the tolylenediamine, a low boiling component, that is, a component rich in water (substantially water) is turned into steam to move to the upper feed tray which is a concentration section of the first column main body 4 while a high boiling component, that is, a component rich in tolylenediamine moves in the form of liquid to the lower feed tray which is a stripping section of the first column main body 4.

Thus, the component rich in tolylenediamine is discharged as the first bottoms from the bottom of the first column main body 4 and the component rich in water is discharged as the first distillate from the top thereof, whereby the fed tolylenediamine having a water content of 5 to 40% by weight is dehydrated.

As for the first bottoms, the ratio of (amount of the first bottoms circulated to the bottom of the first column main body 4 through the first circulation line 12)/(amount of the first bottoms fed to the second-stage distillation column 3 through the first bottoms extraction pipe 9) is set in the range of, for example, 1/1 to 50/1. The above-mentioned circulation amount is appropriately determined according to the form and capacity of the first heater 13.

The first distillate is fed in the form of a first distillate gas (water vapor) from the top of the first column main body 4 to the first cooler 15 through the first distillate extraction pipe 10, and is then cooled and condensed in the first cooler 15. The condensed condensate (water) is discharged as a drainage (wastewater) from the first distillate extraction pipe 10 while a non-condensed gas which has not been condensed is fed to the first vacuum generator 17 through the first vacuum line 16, condensed in the first vacuum generator 17, and finally discharged as a drainage (wastewater).

The first bottoms are tolylenediamine having a water content of, for example, less than 1% by weight, preferably, 0.8% by weight or less, or more preferably 0.5% by weight or less. The first bottoms are extracted at an extraction temperature of, for example, 150 to 250° C.

The first distillate is water containing 0.1% by weight or less of tolylenediamine. The first distillate is discharged at a discharge temperature of, for example, 60 to 100° C. at a discharge rate of 0.5 to 47 m³/h.

The second-stage distillation column 3 is, for example, a continuous distillation column and more specifically includes a second column main body 18, a second reboiler 19, and a second condenser 20.

The second column main body 18 is, for example, a plate column or a packed column, for example, having the same packing materials as those described above packed inside. The second column main body 18 is, if necessary, provided with a distributor, which is not shown, in the midway of its inner portion in the up and down direction. The second column main body 18 is designed with a column diameter of 250 to 2500 mm and 2 to 40 theoretical plates, or more specifically 3 to 20 theoretical plates.

The first bottoms extraction pipe 9 to which the first bottoms are fed from the first-stage distillation column 2 is connected in the midway of the second column main body 18 in the up and down direction. The bottom of the second column main body 18 is connected to a second bottoms extraction pipe 21 for extracting second bottoms which are rich in tolylenediamine. The top of the second column main body 18 is connected to a second distillate extraction pipe 22 for extracting a second distillate which is rich in water.

The second reboiler 19 includes the second bottoms extraction pipe 21, a second bottoms extraction pump 23 interposed in the midway of the second bottoms extraction pipe 21, a second circulation line 24 branching from the second bottoms extraction pipe 21 on the downstream side from the interposed portion of the second bottoms extraction pump 23 to be connected to the bottom of the second column main body 18, and a second heater 25 interposed in the midway of the second circulation line 24.

The second bottoms extraction pump 23 is selected according to the required flow rate of fluid fed and lift as long as the pump is capable of circulating a part of the second bottoms from the bottom of the second column main body 18 to the bottom of the second column main body 18 through the second circulation line 24, and feeding the remainder of the second bottoms as tolylenediamine having a water content of 0.01% by weight or less (preferably a water content of 0.005% by weight or less) from the bottom of the second column main body 18 to the subsequent step or the like through the second bottoms extraction pipe 21, though not particularly limited thereto. Examples thereof include an axial-flow pump, a centrifugal pump, a gear pump, and a diaphragm pump. Among them, a centrifugal pump is preferably used.

The second heater 25 is composed of a heat exchanger and the same heat exchanger as used in the first heater 13 is used, or a wetted-wall heat exchanger or a multi-tubular heat exchanger is preferably used.

A heat medium is fed to the second heater 25, and the amount of the heat medium fed controls the heating temperature of the second heater 25.

In the second reboiler 19, the heating temperature is controlled by the heat medium in the second heater 25 to heat the second bottoms to be circulated through the second circulation line 24 by forced circulation.

For example, a thermo-siphon-type reboiler can also be used as the second reboiler 19. When a thermo-siphon-type reboiler is used as the second reboiler 19, the above-mentioned second bottoms extraction pump 23 is interposed in the second bottoms extraction pipe 21 on the downstream side from the branching portion, though not shown.

The second condenser 20 includes the second distillate extraction pipe 22, a second cooler 27 interposed in the midway of the second distillate extraction pipe 22, a first reflux pipe 28 connected to the second cooler 27 on the downstream side separately from the second distillate extraction pipe 22, and a second vacuum generator 29 interposed in the second distillate extraction pipe 22 on the downstream side from the interposed portion of the second cooler 27.

The second cooler 27 is composed of a heat exchanger and for example, a multi-tubular heat exchanger is used, or a multi-tubular heat exchanger or a plate type heat exchanger is preferably used. A refrigerant is fed to the second cooler 27 and the amount of the refrigerant fed controls the cooling temperature of the second cooler 27.

Examples of the second vacuum generator 29 include vacuum pumps such as a liquid ring vacuum pump, an oil sealed rotary vacuum pump, a Roots vacuum pump, an oil diffusion vacuum pump, a turbo-molecular vacuum pump, cryopump, and a sputter ion pump; and ejectors such as a steam ejector. Among them, a water ring pump as a liquid ring vacuum pump or an ejector is preferably used.

The use of a water ring pump or an ejector allows prevention of mixing of oil into the second distillate. The distillate from the second-stage distillation column 3 and condensed water of the steam discharged from the ejector are mixed, so that all or part of the mixture can be redistilled in the first-stage distillation column 2. Alternatively, the distillate from the second-stage distillation column 3 and the water discharged from the water ring pump are mixed, so that all or part of the mixture can be redistilled in the first-stage distillation column 2.

Further, a water ring pump equipped with an auxiliary vacuum generator, to which an auxiliary vacuum generator is attached, is preferably used as the water ring pump. This attachment of the auxiliary vacuum generator to the water ring pump can improve the ultimate vacuum.

In the second condenser 20, cooling temperature is controlled by the refrigerant in the second cooler 27, and a distillate gas from the top of the second column main body 18 is cooled and condensed to form a condensate rich in water. The second column main body 18 is depressurized through the second distillate extraction pipe 22 and the second cooler 27 from the second vacuum generator 29.

Further, a storage tank 30 is connected to the downstream end portion of the second distillate extraction pipe 22, a second reflux pipe 31 as a reflux units for refluxing the second distillate to the first-stage distillation column 2 is connected to the storage tank 30 on the downstream side, and a second distillate reflux pump 32 is interposed in the midway of the second reflux pipe 31. Further, the downstream end portion of the second reflux pipe 31 is connected to the first column main body 4 of the first-stage distillation column 2.

The storage tank 30 is not particularly limited as long as it is a tank capable of temporarily storing the second distillate until the second distillate is refluxed to the first-stage distillation column 2 through the second reflux pipe 31 by the second distillate reflux pump 32, and for example, a tank having a capacity of 0.1 to 5 m$^3$ is used.

The second distillate reflux pump 32 is selected according to the required flow rate of fluid fed and lift as long as the pump is capable of feeding the second distillate so that the second distillate is refluxed to the first-stage distillation column 2 through the second reflux pipe 31. Examples thereof include a centrifugal pump, a gear pump, and a diaphragm pump. Among them, a centrifugal pump is preferably used.

In the second-stage distillation column 3, the bottom portion of the second column main body 18 is heated by the second reboiler 19, and the top portion thereof is depressurized by the second condenser 20. This sets the temperature at the bottom portion of the second column main body 18 to, for example, 150 to 250° C., the temperature at the top thereof to, for example, 60 to 120° C., and the vacuum degree to less than 13 kPa, or preferably 8 kPa or less.

The first bottoms are fed to the second column main body 18 from the first bottoms extraction pipe 9. The first bottoms are fed, for example, at 0.5 to 47 m$^3$/h.

The first bottoms fed to the second column main body 18 through the first bottoms extraction pipe 9 have a water content of, for example, less than 1% by weight, preferably 0.8% by weight or less, or more preferably 0.5% by weight or less. Of the first bottoms, a low boiling component, that is, a component rich in water (substantially water) is turned into steam to move to the upper feed tray which is a concentration section of the second column main body 18 while a high boiling component, that is, a component rich in tolylenediamine moves in the form of liquid to the lower feed tray which is a stripping section of the second column main body 18.

Thus, the component rich in water is discharged as the second distillate from the top of the second column main body 18 and the component rich in tolylenediamine is discharged as the second bottoms from the bottom of the second column main body 18, whereby the fed tolylenediamine in the first bottoms is further dehydrated.

As for the second bottoms, the ratio of (amount of the second bottoms circulated to the bottom of the second column main body 18 through the second circulation line 24)/(amount of the second bottoms fed to the subsequent step through the second bottoms extraction pipe 21) is set in the range of, for example, 0.5/1 to 50/1. The above-mentioned circulation amount is appropriately determined according to the form and capacity of the second heater 25.

The second distillate is fed in the form of a second distillate gas from the top of the second column main body 18 to the second cooler 27 through the second distillate extraction pipe 22, and is then cooled and condensed in the second cooler 27. The condensed condensate is refluxed as a first reflux liquid to the top of the second column main body 18 through the first reflux pipe 28, a non-condensed gas which has not been condensed is fed to the second vacuum generator 29 through the second distillate extraction pipe 22, condensed in the second vacuum generator 29, and temporarily stored in the storage tank 30 as a second reflux liquid. When the vacuum generator 29 is an ejector (a steam ejector), the noncondensed gas is condensed with drive steam of the ejector.

The second reflux liquid is temporarily stored in the storage tank 30, and thereafter refluxed to the first-stage distillation column 2 through the second reflux pipe 31 as a reflux units.

The reflux ratio for refluxing the condensate as the first reflux liquid is set in the range of, for example, 1/30 to 1/1.

The first reflux liquid is tolylenediamine (hydrous tolylenediamine) having a water content of, for example, 20 to 80% by weight.

The second reflux liquid is tolylenediamine (hydrous tolylenediamine) having a water content of, for example, 5 to 70% by weight, or preferably tolylenediamine (hydrous tolylenediamine) having a water content of 5 to 50% by weight.

The second bottoms are tolylenediamine having a water content of 0.01% by weight or less, or preferably tolylenediamine having a water content of 0.005% by weight or less. The second bottoms are extracted at an extraction temperature of, for example, 150 to 250° C. at an extraction rate of 0.5 to 47 m$^3$/h.

Thus, with the dehydrator 1, first-stage distillation is performed in the first-stage distillation column 2 at a vacuum degree of 13 to 101.3 kPa to dehydrate tolylenediamine at a level at which tolylenediamine does not solidify. Subsequently, second-stage distillation is performed in the second-stage distillation column 3 at a vacuum degree of less than 13 kPa, so that tolylenediamine can be dehydrated until the water content thereof reaches a level required for an intermediate raw material of tolylene diisocyanate. Therefore, the distillation can prevent a solidification zone from being produced and enables tolylenediamine to be dehydrated until the water content thereof reaches a level required for an intermediate raw material of tolylene diisocyanate.

Since the second distillate as the second reflux liquid from the second-stage distillation column 3 is refluxed to the first-stage distillation column 2, the second distillate from the second-stage distillation column 3 is effectively used, so that tolylenediamine remaining in the second distillate can be redistilled in the first-stage distillation column 2.

Further, since the second distillate from the second-stage distillation column 3 is refluxed to the first-stage distillation column 2 through the second reflux pipe 31 without discharging the second distillate as a drainage, the effective use of the second distillate from the second-stage distillation column 3 can achieve reduction in facility cost and operating cost.

Since the water content of the first bottoms from the first-stage distillation column 2 is less than 1% by weight, in the second-stage distillation column 3, tolylenediamine can be dehydrated until the water content thereof reaches a level required for an intermediate raw material of tolylene diisocyanate. The second-stage distillation column 3 can also be designed small in size.

In the first-stage distillation column 2, water is fed to the top of the first column main body 4 of the first-stage distillation column 2 instead of refluxing from a cooling device, to thereby obtain the same effect as the refluxing. Therefore, the steam in the first column main body 4 of the first-stage distillation column 2 can be cooled without providing the first-stage distillation column 2 with a reflux line from the cooling device. As a result, the structure can be simplified, which in turn can achieve improvement in operation, simplification of equipment management, reduction of facility cost, and removal of the tolylenediamine or low-boiling impurities into the first distillate.

In the above explanation, though not shown, for example, when tolylenediamine contains hydrous tolylenediamine as described in the above Patent Document 3, as well as when the need for removing low boiling impurities arises, the second column main body 18 can be provided with a withdrawal apparatus for withdrawing low boiling impurities.

The withdrawal apparatus includes a withdrawal tray, which is not shown, provided in the midway between the top of the second column main body 18 and the first bottoms extraction pipe 9 in the inner portion of the second column main body 18 in the up and down direction to store low boiling impurities, and a withdrawal pipe, which is not shown, connected to the withdrawal tray to withdraw the low boiling impurities stored in the withdrawal tray. If necessary, the withdrawal pipe is provided with a pump in the downstream end portion thereof.

With this withdrawal apparatus, low boiling impurities can be stored in the withdrawal tray of the second column main body 18 and, if necessary, a pump can be used to withdraw the low boiling impurities through the withdrawal pipe.

EXAMPLES

While in the following, the present invention is described in further detail with reference to Example, the present invention is not limited to any of them by no means.

Example 1

As the dehydrator for tolylenediamine as shown in FIG. 1 explained above, a dehydrator 1 including a first-stage distillation column 2 provided with a first column main body 4 packed with packing materials in the column having a diameter of 1000 mm and a length of 10 m; a first reboiler 5 equipped with a first heater 13 composed of a multi-tubuler heat exchanger and a first bottoms extraction pump 11 composed of a centrifugal pump; and a first condenser 6 equipped with a first cooler 15 composed of a multi-tubuler heat exchanger and a first vacuum generator 17 composed of an ejector, a second-stage distillation column 3 provided with a second column main body 18 packed with packing materials in the column having a diameter of 600 mm and a length of 9 m; a second reboiler 19 equipped with a second heater 25 composed of a multi-tubuler heat exchanger and a second bottoms extraction pump 23 composed of a centrifugal pump; and a second condenser 20 equipped with a second cooler 27 composed of a multi-tubuler heat exchanger and a second vacuum generator 29 composed of an ejector, a storage tank 30, a second distillate reflux pump 32 composed of a centrifugal pump, and a second reflux pipe 31 was used.

With this dehydrator 1, tolylenediamine (hydrous tolylenediamine) having a water content of 10% by weight was subjected to dehydration.

In the first-stage distillation column 2, the temperature at the bottom of the first column main body 4 was set to 185° C., the temperature at the top thereof was set to 76° C., and the vacuum degree was set to 40 kPa.

The tolylenediamine having a water content of 10% by weight was fed from a hydrous tolylenediamine feed pipe 7 to the first column main body 4 at a feed temperature of 100° C. with a feed rate of 10 m³/h. Water was also fed to the top portion of the first column main body 4 from a water feed pipe 8 at a feed temperature of 30° C. with a feed rate of 0.1 m³/h.

First bottoms were withdrawn from the bottom of the first column main body 4 through the first bottoms extraction pump 11 at 185° C. When the water content of the first bottoms was determined by toluene azeotropic distillation, the value was 0.5% by weight.

In the second-stage distillation column 3, the temperature at the bottom of the second column main body 18 was set to 200° C., the temperature at the top thereof was set to 82° C., and the vacuum degree was set to 6.67 kPa.

The first bottoms from the bottom of the first column main body 4 were fed to the second column main body 18 through the first bottoms extraction pipe 9 at a feed temperature of 185° C. with a feed rate of 9.05 m³/h.

Second bottoms from the bottom of the second column main body 18 were withdrawn by the second bottoms extraction pump 23 at 200° C. with 9.0 m³/h. When the water content of the second bottoms was determined by toluene azeotropic distillation, the value was 0.003% by weight.

A second distillate gas was extracted from the top of the second column main body 18 at an extraction temperature of, for example, 82° C. with an extraction rate of 0.55 m³/h. This second distillate gas was condensed in the second cooler 27, and a first reflux liquid thus condensed was refluxed to the second column main body 18 through a first reflux pipe 28.

In the second cooler 27, a non-condensed gas which had not been condensed was condensed in the second vacuum generator 29 composed of an ejector, and a second reflux liquid thus condensed was refluxed from the second reflux pipe 31 to the first column main body 4 of the first-stage distillation column 2. When the water content of the second reflux liquid was determined by gas chromatography, the value was 80% by weight.

The reflux ratio for refluxing as the first reflux liquid was set to 1/10.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The tolylenediamine obtained by the method of dehydrating tolylenediamine and the dehydrator according to the present invention is used for production of tolylene diisocyanate as a raw material of polyurethane.

The invention claimed is:

1. A method of dehydrating tolylenediamine, comprising:
subjecting tolylenediamine having a water content of 5 to 40% by weight to first-stage distillation at a vacuum degree of 13 to 101.3 kPa,
subjecting bottoms from the first-stage distillation to second-stage distillation at a vacuum degree of less than 13 kPa, and
refluxing the distillate from the second-stage distillation set to have a water content of 5 to 70% by weight to the first-stage distillation.

2. The method of dehydrating tolylenediamine according to claim 1, wherein the bottoms from the first-stage distillation has a water content of less than 1% by weight.

3. The method of dehydrating tolylenediamine according to claim 1, wherein water is fed to a top portion of a first-stage distillation column in the first-stage distillation.

4. The method of dehydrating tolylenediamine according to claim 1, wherein an ejector or a water ring pump is used as a vacuum generator for depressurizing in the second-stage distillation.

* * * * *